(12) United States Patent
Bayer (10) Patent No.: US 8,064,666 B2
(45) Date of Patent: Nov. 22, 2011

(54) METHOD AND DEVICE FOR EXAMINING OR IMAGING AN INTERIOR SURFACE OF A CAVITY

(75) Inventor: Lex Bayer, Palo Alto, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 865 days.

(21) Appl. No.: 12/101,050

(22) Filed: Apr. 10, 2008

(65) Prior Publication Data

US 2008/0253686 A1  Oct. 16, 2008

Related U.S. Application Data

(60) Provisional application No. 60/911,054, filed on Apr. 10, 2007.

(51) Int. Cl.
*G06K 9/00* (2006.01)
*G06K 9/36* (2006.01)
(52) U.S. Cl. ........................ 382/128; 382/284
(58) Field of Classification Search .......... 382/128–134, 382/284
See application file for complete search history.

(56) References Cited

U.S. PATENT DOCUMENTS

| | | | |
|---|---|---|---|
| 3,610,231 A | 10/1971 | Takahashi et al. |
| 3,643,653 A | 2/1972 | Takahashi et al. |
| 3,739,770 A | 6/1973 | Mori |
| 3,897,775 A | 8/1975 | Furihata |
| 4,261,344 A | 4/1981 | Moore et al. |
| 4,573,450 A | 3/1986 | Arakawa |
| 4,586,491 A | 5/1986 | Carpenter |
| 4,625,236 A | 11/1986 | Fujimori et al. |
| 4,646,722 A | 3/1987 | Silverstein et al. |
| 4,721,097 A | 1/1988 | D'Amelio |
| 4,741,326 A | 5/1988 | Sidall et al. |
| 4,800,870 A | 1/1989 | Reid, Jr. |
| 4,825,850 A | 5/1989 | Opie et al. |
| 4,852,551 A | 8/1989 | Opie et al. |
| 4,869,238 A | 9/1989 | Opie et al. |
| 4,870,488 A | 9/1989 | Ikuno et al. |
| 4,873,965 A | 10/1989 | Danieli |
| 4,899,732 A | 2/1990 | Cohen |
| 4,905,667 A | 3/1990 | Foerster et al. |
| 4,907,395 A | 3/1990 | Opie et al. |
| 4,911,564 A | 3/1990 | Baker |
| 4,947,827 A | 8/1990 | Opie et al. |

(Continued)

FOREIGN PATENT DOCUMENTS

CN   1 628 603   6/2005

(Continued)

OTHER PUBLICATIONS

U.S. Appl. No. 11/736,438, filed Apr. 17, 2007, Bayer.

(Continued)

*Primary Examiner* — Brian Werner
*Assistant Examiner* — Utpal Shah
(74) *Attorney, Agent, or Firm* — Morrison & Foerster LLP (57) ABSTRACT

A method for examining an interior surface of a cavity includes the steps of capturing partial images of an interior surface of a cavity; joining the captured partial images to form a complete image of said interior surface of the cavity; and providing an warning if the joined partial images does not form a complete image of said interior surface of the cavity.

52 Claims, 6 Drawing Sheets

U.S. PATENT DOCUMENTS

| | | | |
|---|---|---|---|
| 4,979,496 | A | 12/1990 | Komi |
| 4,991,565 | A | 2/1991 | Takahashi et al. |
| 5,019,040 | A | 5/1991 | Itaoka et al. |
| 5,025,778 | A | 6/1991 | Silverstein et al. |
| 5,050,585 | A | 9/1991 | Takahashi |
| RE34,110 | E | 10/1992 | Opie et al. |
| 5,166,787 | A | 11/1992 | Irion |
| 5,178,130 | A | 1/1993 | Kaiya et al. |
| 5,193,525 | A | 3/1993 | Silverstein et al. |
| 5,271,381 | A | 12/1993 | Ailinger et al. |
| 5,329,887 | A | 7/1994 | Ailinger et al. |
| 5,337,734 | A | 8/1994 | Saab |
| 5,443,781 | A | 8/1995 | Saab |
| 5,447,148 | A | 9/1995 | Oneda et al. |
| 5,483,951 | A | 1/1996 | Frassica et al. |
| 5,518,501 | A | 5/1996 | Oneda et al. |
| 5,520,607 | A | 5/1996 | Frassica et al. |
| 5,533,496 | A | 7/1996 | De Faria-Correa et al. |
| 5,536,236 | A | 7/1996 | Yabe et al. |
| 5,626,553 | A | 5/1997 | Frassica et al. |
| 5,667,476 | A | 9/1997 | Frassica et al. |
| 5,679,216 | A | 10/1997 | Takayama et al. |
| 5,685,822 | A | 11/1997 | Harhen |
| 5,692,729 | A | 12/1997 | Harhen |
| 5,702,348 | A | 12/1997 | Harhen |
| 5,722,933 | A | 3/1998 | Yabe et al. |
| 5,752,912 | A | 5/1998 | Takahashi et al. |
| 5,762,603 | A | 6/1998 | Thompson |
| 5,827,177 | A | 10/1998 | Oneda et al. |
| 5,860,914 | A | 1/1999 | Chiba et al. |
| 5,876,329 | A | 3/1999 | Harhen |
| 5,916,147 | A | 6/1999 | Boury |
| 5,924,977 | A | 7/1999 | Yabe et al. |
| 5,989,182 | A | 11/1999 | Hori et al. |
| 6,017,358 | A | 1/2000 | Yoon |
| 6,066,090 | A | 5/2000 | Yoon |
| 6,099,464 | A | 8/2000 | Shimizu et al. |
| 6,099,485 | A | 8/2000 | Patterson |
| 6,174,280 | B1 | 1/2001 | Oneda et al. |
| 6,190,330 | B1 | 2/2001 | Harhen |
| 6,214,028 | B1 | 4/2001 | Yoon et al. |
| 6,261,226 | B1 | 7/2001 | McKenna et al. |
| 6,261,307 | B1 | 7/2001 | Yoon et al. |
| 6,277,064 | B1 | 8/2001 | Yoon |
| 6,350,231 | B1 | 2/2002 | Ailinger et al. |
| 6,461,294 | B1 | 10/2002 | Oneda et al. |
| 6,547,724 | B1 | 4/2003 | Soble et al. |
| 6,736,773 | B2 | 5/2004 | Wendlandt et al. |
| 6,748,975 | B2 | 6/2004 | Hartshorne et al. |
| 6,845,190 | B1 | 1/2005 | Smithwick et al. |
| 6,974,411 | B2 | 12/2005 | Belson |
| 7,004,900 | B2 | 2/2006 | Wendlandt et al. |
| 7,029,435 | B2 | 4/2006 | Nakao |
| 2002/0039400 | A1 | 4/2002 | Kaufman et al. |
| 2002/0156347 | A1 | 10/2002 | Kim et al. |
| 2002/0193662 | A1 | 12/2002 | Belson |
| 2003/0004399 | A1 | 1/2003 | Belson |
| 2003/0032863 | A1 | 2/2003 | Kazakevich |
| 2003/0040668 | A1 | 2/2003 | Kaneko et al. |
| 2003/0065250 | A1 | 4/2003 | Chiel et al. |
| 2003/0088152 | A1 | 5/2003 | Takada |
| 2003/0093031 | A1 | 5/2003 | Long et al. |
| 2003/0093088 | A1 | 5/2003 | Long et al. |
| 2003/0105386 | A1 | 6/2003 | Voloshin et al. |
| 2003/0120130 | A1 | 6/2003 | Glukhovsky |
| 2003/0125788 | A1 | 7/2003 | Long |
| 2003/0153866 | A1 | 8/2003 | Long et al. |
| 2003/0171650 | A1 | 9/2003 | Tartaglia et al. |
| 2003/0187326 | A1 | 10/2003 | Chang |
| 2003/0195545 | A1 | 10/2003 | Hermann et al. |
| 2003/0225433 | A1 | 12/2003 | Nakao |
| 2003/0233115 | A1 | 12/2003 | Eversull et al. |
| 2004/0034278 | A1 | 2/2004 | Adams |
| 2004/0049096 | A1 | 3/2004 | Adams |
| 2004/0059191 | A1 | 3/2004 | Krupa et al. |
| 2004/0080613 | A1 | 4/2004 | Moriyama |
| 2004/0111019 | A1 | 6/2004 | Long |
| 2004/0141054 | A1 | 7/2004 | Mochida et al. |
| 2005/0010084 | A1 | 1/2005 | Tsai |
| 2005/0038317 | A1 | 2/2005 | Ratnakar |
| 2005/0085693 | A1 | 4/2005 | Belson et al. |
| 2005/0085790 | A1 | 4/2005 | Guest et al. |
| 2005/0165272 | A1 | 7/2005 | Okada et al. |
| 2005/0228224 | A1 | 10/2005 | Okada et al. |
| 2005/0272975 | A1 | 12/2005 | McWeeney et al. |
| 2005/0272977 | A1 | 12/2005 | Saadat et al. |
| 2006/0106286 | A1 | 5/2006 | Wendlandt et al. |
| 2006/0149129 | A1 | 7/2006 | Watts et al. |
| 2006/0183975 | A1 | 8/2006 | Saadat et al. |
| 2006/0293562 | A1 | 12/2006 | Uchimura et al. |
| 2007/0103460 | A1* | 5/2007 | Zhang et al. ................ 345/419 |
| 2007/0142711 | A1 | 6/2007 | Bayer et al. |
| 2007/0177008 | A1 | 8/2007 | Bayer et al. |
| 2007/0177009 | A1 | 8/2007 | Bayer et al. |
| 2007/0183685 | A1* | 8/2007 | Wada et al. ................ 382/285 |
| 2007/0185384 | A1 | 8/2007 | Bayer et al. |
| 2007/0270642 | A1 | 11/2007 | Bayer |
| 2007/0279486 | A1 | 12/2007 | Bayer et al. |
| 2007/0293720 | A1 | 12/2007 | Bayer |
| 2008/0021274 | A1 | 1/2008 | Bayer et al. |
| 2008/0199829 | A1* | 8/2008 | Paley et al. ................ 433/215 |

FOREIGN PATENT DOCUMENTS

| | | |
|---|---|---|
| DE | 196 26 433 | 1/1998 |
| EP | 0 586 162 | 3/1994 |
| WO | WO 93/15648 | 8/1993 |

OTHER PUBLICATIONS

International Search Report for PCT/US2005/044624, filed Dec. 8, 2005, mailed May 19, 2006, 16 pgs.

International Search Report for PCT/US2006/047748, filed Dec. 13, 2006, mailed Jun. 20, 2007, 12 pgs.

Invitation to Pay Additional Fees for PCT/US2007/002096, filed Jan. 23, 2007, mailed Jul. 6, 2007, 4 pgs.

Invitation to Pay Additional Fees for PCT/US2007/003631, filed Feb. 9, 2007, mailed Aug. 7, 2007, 5 pgs.

Invitation to Pay Additional Fees for PCT/US2007/003322, filed Feb. 6, 2007, mailed Aug. 7, 2007, 6 pgs.

International Search Report for PCT/US2008/069435, filed Jul. 8, 2008, mailed Oct. 23, 2008, 8 pgs.

Invitation to Pay Additional Fees for PCT/US2008/071390, filed Jul. 28, 2008, mailed Nov. 11, 2008, 5 pgs.

* cited by examiner

METHOD AND DEVICE FOR EXAMINING OR IMAGING AN INTERIOR SURFACE OF A CAVITY

This application claims the benefit of U.S. Provisional Patent Application No. 60/911,054, filed Apr. 10, 2007, the entire disclosure of which is incorporated herein by reference.

TECHNICAL FIELD OF THE INVENTION

The present invention relates to a method and device for examining or imaging an interior surface of a cavity such as a colon.

BACKGROUND OF THE INVENTION

A scope is often used to view and examine the interior of a cavity. An endoscope is a medical device comprising a flexible tube, which is insertable into an internal body cavity through a body orifice to examine the body cavity and tissues for diagnosis. An endoscope may include a camera and a light source mounted on the distal end of its flexible tube to allow visualization of the internal environment of the body cavity. The tube of the endoscope has one or more longitudinal channels, through which an instrument can reach the body cavity to take samples of suspicious tissues or to perform other surgical procedures such as polypectomy.

To insert an endoscope into an internal body cavity, a physician advances the endoscope's flexible tube into the body cavity with the distal end of the flexible tube at the front. The physician may steer the flexible tube to follow the cavity's contour by controlling a bendable distal end portion of the flexible tube. After the endoscope is advanced to the end of the colon, the physician begins to retract the endoscope and visually scans the colon for abnormalities as the endoscope is retracted.

It is important for the physician to examine all areas of the colon where abnormalities may occur. Failure to do so may have grave consequences. However, it is difficult for the physician to simultaneously focus on examining the colon and keep track of the areas that have not been examined (or the areas of the colon that have been examined). Therefore, it is desirable to have a device or method that assists the physician in keeping track of the unexamined areas of the colon (or the examined areas).

Additionally, to ensure a careful examination of the colon, it is desirable to monitor the amount of time the physician spends examining an area of the colon, and to warn the physician if she spends insufficient time examining the area.

SUMMARY OF THE INVENTION

According to one embodiment of the present invention, an endoscope may be used to examine or image an interior surface of a cavity such as a colon. To examine (or image) a colon, for example, an operator such as a physician may first advance the endoscope to the end of the colon or to a point beyond an area of the colon to be examined. Then the operator may retract the endoscope and start examining the colon by viewing the partial images of the colon captured by the imaging device of the endoscope. The partial images captured by the imaging device are relayed to a video processing device that joins the partial images to generate a two dimensional image of the colon's interior surface. If the video processing device cannot generate a single complete view of the colon's interior surface (i.e. an area of the colon is missing from the single view), it emits a warning signal, which communicates to the physician that an area of the colon's interior surface has been missed. The physician can then move the imaging device to the missing area and capture one or more additional images. The video processing device can then integrate the additional images into the single image of the colon's interior surface. At the end of the procedure, the processing device has created a complete two-dimensional image of the colon's interior surface.

According to another embodiment of the invention, the video processing device can calculate the scanning speed and/of the total amount of time that the imaging device spends in a segment of the colon such as the ascending or transverse portion of the colon. This information can also be used to warn the physician of potential hasty examination. Those and other embodiments of the present invention overcome the disadvantages associated with the prior art.

The following is a more detailed description of some features of the present invention's embodiments. According to one aspect of the invention, a method for examining or imaging an interior surface of a cavity includes the steps of capturing partial images of an interior surface of a cavity; joining the captured partial images to form a complete image of said interior surface of the cavity; and providing an warning if the joined partial images does not form a complete image of said interior surface of the cavity.

In one preferred embodiment, the step of capturing partial images includes the steps of storing the captured partial images; and recording a sequence in which the partial images were captured.

In another preferred embodiment, the cavity is a tubular cavity and each partial image is a partial image of said interior surface of the tubular cavity. And the step of joining the captured partial images includes flattening the partial images of the interior surface of the tubular cavity; and joining the flattened partial images to form a complete flat image of said interior surface of the tubular cavity.

In still another preferred embodiment, the step of flattening each partial image includes outlining the lumen of the tubular cavity in said partial image by analyzing said partial image for the difference in contrast between the lumen of the tubular cavity and said interior surface of the tubular cavity; and excising the lumen from said partial image.

In yet another preferred embodiment, the step of flattening each partial image includes excising an outer edge of the tubular cavity in said partial image.

In still yet another preferred embodiment, the excised outer edge of said interior surface of the tubular cavity is larger than, but similar in shape to, the excised lumen.

In another preferred embodiment, the tubular cavity is a colon, and the excised outer edge of the interior surface of the colon is an outline of a haustral fold of the colon.

In a further preferred embodiment, the step of flattening each partial image includes flattening the excised partial image to create a rectangular image.

In a still further preferred embodiment, the step of flattening the excised partial image to create a rectangular image includes straightening each of the inner and outer edges of said interior surface of the tubular cavity into a substantially straight line.

In a yet further preferred embodiment, the step of joining the captured partial images includes identifying similar regions or corresponding key points between any two images.

In a yet still further preferred embodiment, the step of joining the captured partial images includes calculating a suitable transformation matrix which brings the any two images together such that the key points or similar regions overlap.

In another preferred embodiment, the step of joining the captured partial images includes joining the two images by meshing or overlapping the images as dictated by the transformation matrix.

In still another preferred embodiment, the method further includes capturing one or more additional partial images of a missing area in the image of the interior surface of the cavity if the joined partial images does not form a complete image of said interior surface of the cavity; joining the one or more additional partial images with the incomplete image of said interior surface of the cavity to form a complete image of said interior surface of the cavity; and providing an warning if the joined partial images still does not form a complete image of said interior surface of the cavity.

In yet another preferred embodiment, the method further includes providing direction to an operator to reach the missing area.

In yet still another preferred embodiment, the step of providing direction includes using an on-screen navigation cue to direct an operator to the missing area.

In a further preferred embodiment, the on-screen navigation cue includes an arrow and the missing area, both of which are displayed on a screen.

In a further preferred embodiment, the method further includes calculating a scanning speed.

In a still further preferred embodiment, the step of calculating the scanning speed includes identifying similar regions or corresponding key points between any two images; calculating a distance by which a key point or corresponding area has moved from the earlier one of the two images to the later of the two images; and calculating the scanning speed by dividing the distance by the time lapsed between the two images.

In a yet further preferred embodiment, the step of calculating the distance includes counting the number of image pixels by which the key point or corresponding area has moved.

In another preferred embodiment, the method further includes providing a warning if the scanning speed is greater than a given value.

In still another preferred embodiment, the method further includes calculating an amount of time spent on examining a region of said interior surface of the cavity.

In yet another preferred embodiment, the method further includes recognizing known features of said interior surface of the cavity to determine the region being examined.

In a further preferred embodiment, the method further includes providing a warning if the amount of time spent on examining the region is less than a given value.

According to another aspect of the invention, a method for examining or imaging an interior surface of a cavity includes capturing partial images of an interior surface of a cavity; joining the captured partial images to form a complete image of said interior surface of the cavity; capturing one or more additional partial images of a missing area in the image of said interior surface of the cavity if the joined partial images does not form a complete image of said interior surface of the cavity; and joining the one or more additional partial images with the incomplete image of said interior surface of the cavity to form a complete image of said interior surface of the cavity.

In a preferred embodiment, the method further includes providing direction to an operator to reach the missing area.

In another preferred embodiment, the step of providing direction includes using an on-screen navigation cue to direct an operator to the missing area.

In still another preferred embodiment, the on-screen navigation cue includes an arrow and the missing area, both of which are displayed on a screen.

According to still another aspect of the invention, a method for examining or imaging an interior surface of a colon includes capturing partial images of an interior surface of a colon; and joining the captured partial images to form a complete image of said interior surface of the colon.

In a preferred embodiment, each partial image is a partial image of said interior surface of the colon, and the step of joining the captured partial images includes flattening the partial images of the interior surface of the colon; and joining the flattened partial images to form a complete flat image of said interior surface of the colon.

In another preferred embodiment, the step of flattening each partial image includes outlining the lumen of the colon in said partial image by analyzing said partial image for the difference in contrast between the lumen of the colon and said interior surface of the colon; and excising the lumen from said partial image.

In still another preferred embodiment, the step of flattening each partial image includes excising an outer edge of the colon in said partial image.

In yet another preferred embodiment, the excised outer edge of said interior surface of the colon is larger than, but similar in shape to, the excised lumen.

In a further preferred embodiment, the excised outer edge of the interior surface of the colon is an outline of a haustral fold of the colon.

In a still further preferred embodiment, the step of flattening each partial image includes flattening the excised partial image to create a rectangular image.

In a yet further preferred embodiment, the step of flattening the excised partial image to create a rectangular image includes straightening each of the inner and outer edges of said interior surface of the colon into a substantially straight line.

In a yet still further preferred embodiment, the step of joining the captured partial images includes identifying similar regions or corresponding key points between any two images.

In another preferred embodiment, the step of joining the captured partial images includes calculating a suitable transformation matrix which brings the two images together such that the key points or similar regions overlap.

In still another preferred embodiment, wherein the step of joining the captured partial images includes joining the two images by meshing or overlapping the images as dictated by the transformation matrix.

In yet another preferred embodiment, the method further includes providing an warning if the joined partial images does not form a complete image of said interior surface of the colon.

In yet still another preferred embodiment, the method further includes capturing one or more additional partial images of a missing area in the image of the interior surface of the colon if the joined partial images does not form a complete image of said interior surface of the colon; joining the one or more additional partial images with the incomplete image of said interior surface of the colon to form a complete image of said interior surface of the colon; and providing an warning if the joined partial images still does not form a complete image of said interior surface of the colon.

In a further preferred embodiment, the method further includes providing an warning if the joined partial images does not form a complete image of said interior surface of the colon.

In another preferred embodiment, the method further includes capturing one or more additional partial images of a missing area in the image of the interior surface of the colon if the joined partial images does not form a complete image of said interior surface of the colon; joining the one or more additional partial images with the incomplete image of said interior surface of the colon to form a complete image of said interior surface of the colon; and providing an warning if the joined partial images still does not form a complete image of said interior surface of the colon.

According to yet another aspect of the invention, a method for examining or imaging an interior surface of a colon includes visually scanning an interior surface of a colon; calculating a scanning speed; and providing a warning if the scanning speed is greater than a given value.

In another preferred embodiment, the step of calculating the scanning speed includes capturing partial images of said interior surface of a colon; identifying similar regions or corresponding key points between any two images; calculating a distance by which a key point or corresponding area has moved from the earlier one of the two images to the later of the two images; and calculating the scanning speed by dividing the distance by the time lapsed between the two images.

In still another preferred embodiment, the step of calculating the distance includes counting the number of image pixels by which the key point or corresponding area has moved.

According to a further aspect of the invention, a method for examining an interior surface of a colon includes visually scanning an interior surface of a colon; and calculating an amount of time spent on examining a region of said interior surface of the colon.

In another preferred embodiment, the method further includes recognizing known features of said interior surface of the colon to determine the region being examined.

In a further preferred embodiment, the method further includes providing a warning if the amount of time spent on examining the region is less than a given value.

According to a further aspect of the invention, a device for examining or imaging an interior surface of a cavity includes an element for capturing partial images of an interior surface of a cavity; an element for joining the captured partial images to form a complete image of said interior surface of the cavity; and an element for providing an warning if the joined partial images does not form a complete image of said interior surface of the cavity.

According to a still further aspect of the invention, a device for examining or imaging an interior surface of a cavity includes an element capturing partial images of an interior surface of a cavity; an element joining the captured partial images to form a complete image of said interior surface of the cavity; an element capturing one or more additional partial images of a missing area in the image of said interior surface of the cavity if the joined partial images does not form a complete image of said interior surface of the cavity; and an element joining the one or more additional partial images with the incomplete image of said interior surface of the cavity to form a complete image of said interior surface of the cavity.

According to a yet further aspect of the invention, a device for examining or imaging an interior surface of a colon includes an element capturing partial images of an interior surface of a colon; and an element joining the captured partial images to form a complete image of said interior surface of the colon.

DETAILED DESCRIPTION OF EMBODIMENTS OF THE INVENTION

According to one embodiment of the present invention, an endoscope may be used to examine or image an interior surface of a cavity such as a colon. To examine (or image) a colon, for example, an operator such as a physician may first advance the endoscope to the end of the colon or to a point beyond an area of the colon to be examined. Then the operator may retract the endoscope and start examining the colon by viewing the partial images of the colon captured by the imaging device of the endoscope. The partial images captured by the imaging device are relayed to a video processing device that joins, either in real time or subsequent to a colon examination, the partial images to generate a complete two-dimensional image of the colon's interior surface. If the video processing device cannot generate a complete view of the colon's interior surface, it emits a warning signal, which communicates to the physician that an area of the colon's interior surface has been missed. The physician can then move the imaging device to the missing area and capture one or more additional images. The video processing device can then integrate the additional images into the two dimensional image of the colon's interior surface. At the end of the procedure, the processing device has created a complete two-dimensional image of the colon's interior surface.

The complete image of the colon's interior surface may be used for various purposes. For example, a series of complete images of the colon's interior surface may be obtained and stored over a period of time. A newer image may be compared an older image to determine whether there have been any new polyps or whether there has been any enlargement of a polyps. Additionally, stored images may be used to prove in a malpractice lawsuit that the physician did not miss a polyps during a colon examination.

Figure 1:
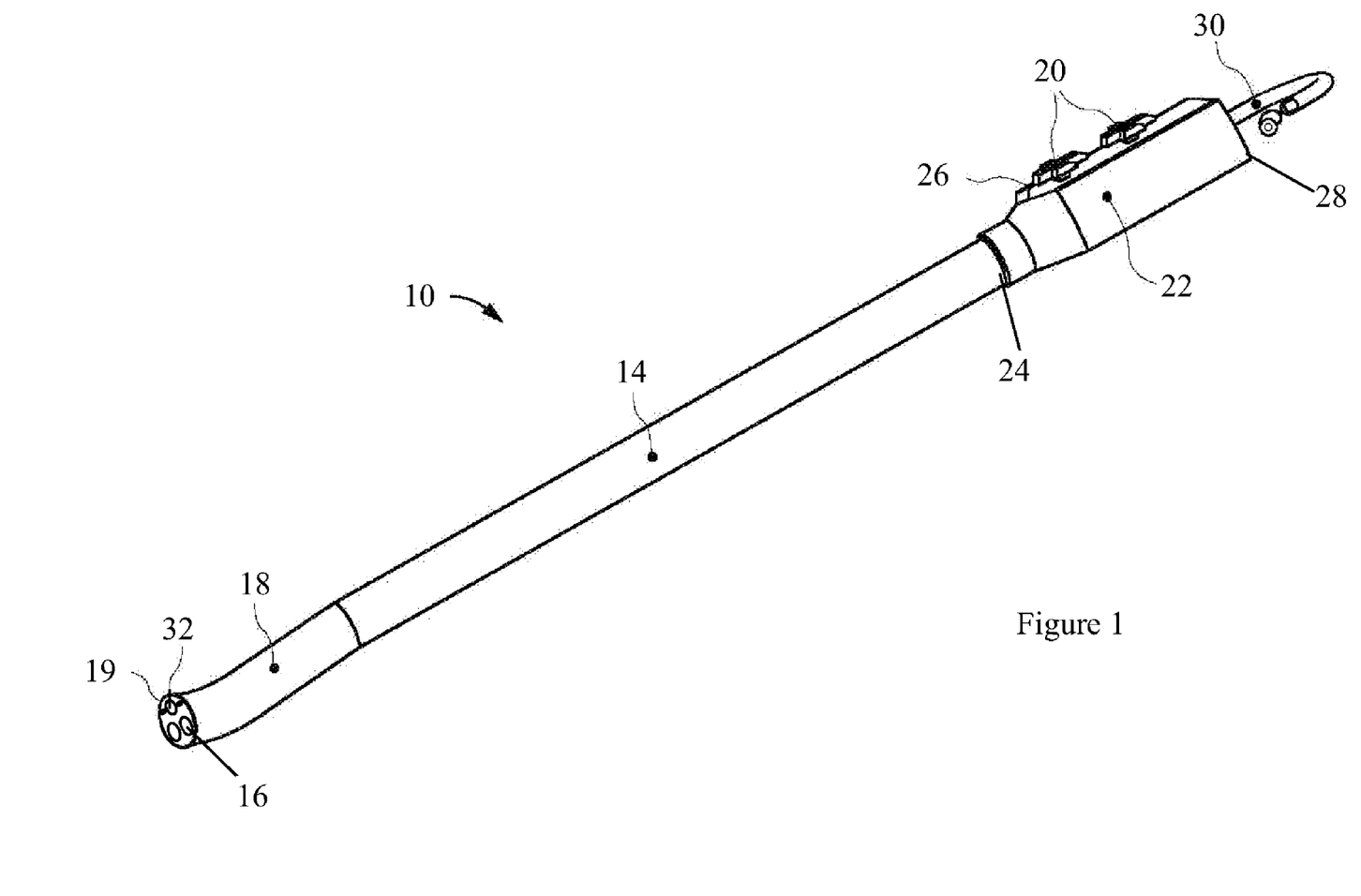
FIG. 1 shows a perspective view of an endoscope that can be used with the present invention.

FIG. 1 illustrates an exemplary endoscope 10 that can be used with one or more embodiments of the present invention. In particular, this endoscope 10 can be used in the examining or imaging of the interior surface of a cavity. For example, the endoscope 10 can be used in a variety of medical procedures in which examining or imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

Figure 2:
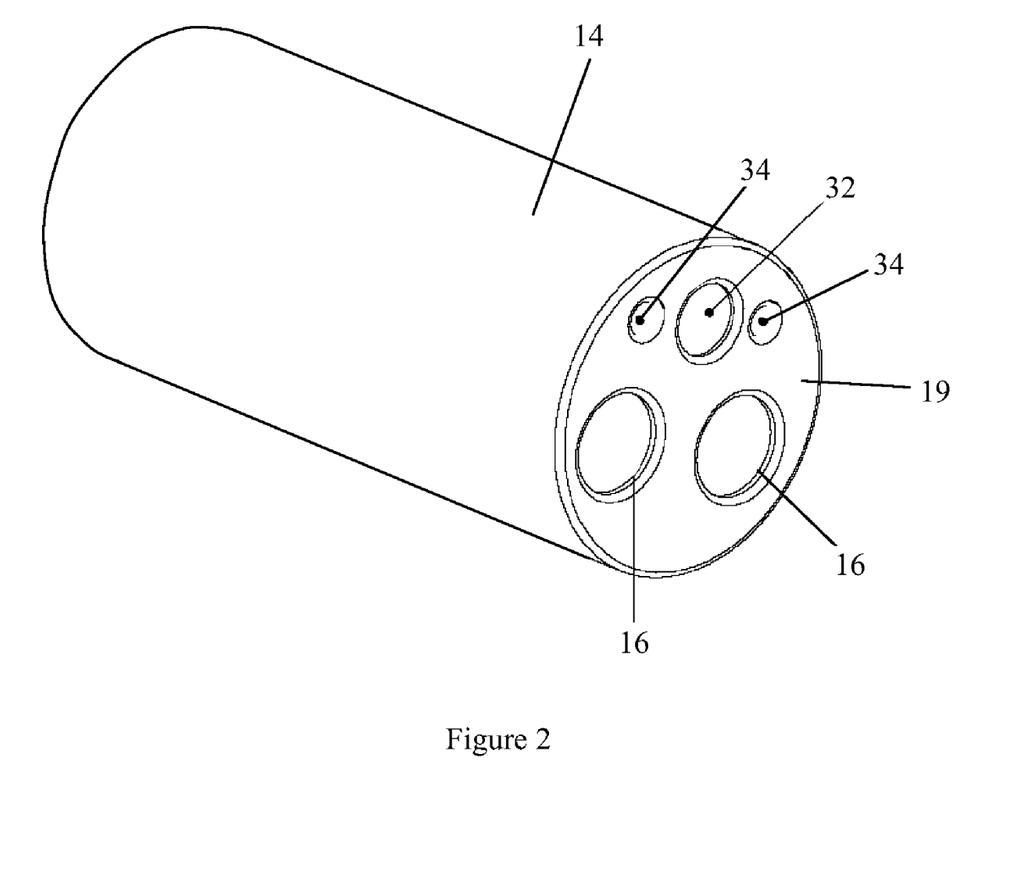
FIG. 2 shows a perspective view of the distal end of an insertion tube of the endoscope of FIG. 1.

The endoscope 10 includes an insertion tube 14 that, as shown in FIG. 2, has two longitudinal channels 16. In general, however, the insertion tube 14 may have any number of longitudinal channels. Each longitudinal channel 16 allows an instrument to reach the body cavity to perform any desired procedures such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract liquids or inject liquids, such as a drug in a liquid carrier, into the body.

The insertion tube 14 preferably is steerable or has a steerable distal end region 18 as shown in FIG. 1. The length of the distal end region 18 may be any suitable fraction of the length of the insertion tube 14, such as one half, one third, one fourth, one sixth, one tenth, or one twentieth. The insertion tube 14 may have control cables (not shown) for the manipulation of the insertion tube 14. Preferably, the control cables are symmetrically positioned within the insertion tube 14 and extend along the length of the insertion tube 14. The control cables may be anchored at or near the distal end 19 of the insertion tube 14. Each of the control cables may be a Bowden cable, which includes a wire contained in a flexible overlying hollow tube. The wires of the Bowden cables are attached to controls 20 in the handle 22 (FIG. 1). Using the controls 20, the wires can be pulled to bend the distal end region 18 of the insertion tube 14 in a given direction.

As shown in FIG. 1, the endoscope 10 may also include a control handle 22 connected to the proximal end 24 of the insertion tube 14. Preferably, the control handle 22 has one or more ports and/or valves (not shown) for controlling access to the channels 16 of the insertion tube 14. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 14.

The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

As shown in FIG. 2, the endoscope 10 also includes an imaging device 32 and light sources 34, both of which are disposed at the distal end 19 of the insertion tube 14. Alternatively, the imaging device 32 and light source 34 may be positioned on the cylindrical sidewall of the insertion tube 14. The imaging device 32 may include, for example, a lens, single chip sensor, multiple chip sensor or fiber optic implemented devices. The imaging device 32, in electrical communication with a processor and/or monitor, may provide still images or recorded or live video images. The light sources 34 may be light emitting diodes (LEDs) or fiber optical delivery of light from an external light source. The light sources 34 preferably are equidistant from the imaging device 32 to provide even illumination. The intensity of each light source 34 can be adjusted to achieve optimum imaging. The circuits for the imaging device 32 and light sources 34 may be incorporated into a printed circuit board (PCB).

According to one embodiment of the present invention, this endoscope 10 may be used to examine or image an interior surface of a cavity such as a colon. To examine (or image) a colon, for example, an operator such as a physician may insert the endoscope 10 into the patient's rectum and then advance it to the end of the colon or to a point beyond an area of the colon to be examined. Then the operator may retract the endoscope 10 and start examining the colon by viewing the images captured by the imaging device 32 of the endoscope 10. Alternatively, the operator may examine the colon by advancing the endoscope 10 (as opposed to retracting the endoscope 10). In general, the operator may move or position the endoscope 10 in any suitable manner during the examination of the colon.

As the colon is being examined, partial still images of the colon are captured. The still images may be captured from the video signal generated by the imaging device 32. Alternatively, a still camera may be used to capture the images. The still images may be captured either automatically or manually. To manually capture the partial still images, the operator may decide when a still image is captured by pressing a button. Manual operation has the advantage that an image is captured only when the view is sufficient clear and when there is no fluid or excrement in the view that prevents an unobstructed view of the colon's interior surface. If there is fluid or secretion in the view, the operator may wash the colon or extract the fluid or secretion from the colon before an image is captured. The images captured by the imaging device 32 are then relayed to a processing device, which stores the images in memory. Preferably the order in which the images are captured is also stored.

Given the image capture rate of a typical imaging device, it may be unnecessary to store and use every image in order to obtain the complete two-dimensional image of the colon's interior surface. Accordingly, an image that is blurry or difficult to join may be discarded and the next image may be stored and used. A blurry image may be caused by fluid or excrement in the colon. In addition, when the imaging device 32 is paused at a location, duplicate or similar images can be discarded such that unnecessary images are not stored and used to form the final joined image. For example, if a procedure such as a biopsy or polypectomy needs to be performed using the endoscope, the physician can pause the image capture such that the final joined image is not adversely affected. Furthermore, the operator can decide whether images are being collected merely for display, for creating the final joined image, or both.

Figure 3A:
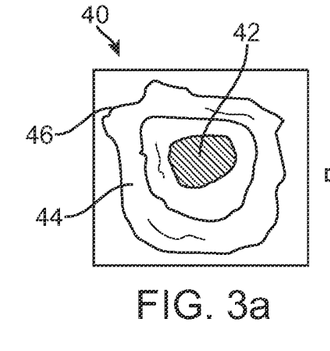
FIGS. 3a to 3g show an example of image transformation.

If the imaging device 32 is disposed at the distal end 19 of the insertion tube 14, the imaging device 32 faces the longitudinal direction of the colon, and the image of the colon captured by the imaging device 32 will likely show a view of the colon's interior surface along the longitudinal direction. In other words, as shown in FIG. 3a, the captured view of the colon 40 will likely show the colon's lumen 42 surrounded by the colon's interior surface 44, with the colon's interior surface 44 farther away from the imaging device 32 being at the center of the image 40 and surrounding the colon's lumen 42 and with the colon's interior surface 44 closer to the imaging device 32 being at the outer edge of the image 40.

Figure 3B:
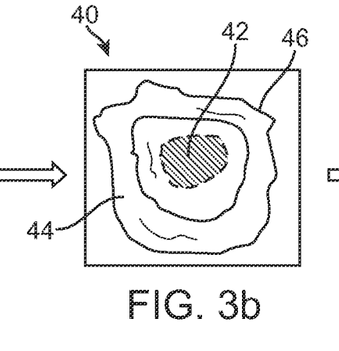
Figure 3C:
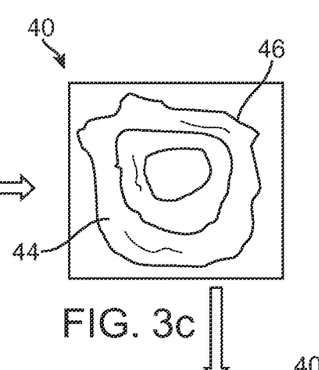
Figure 3D:
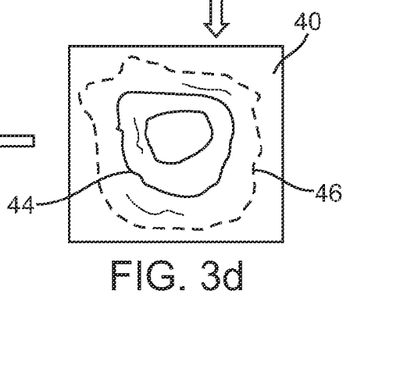
Figure 3E:
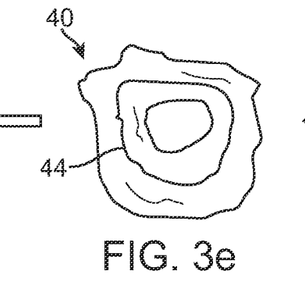

In some embodiments of the present invention, after an image of the colon has been captured and relayed to the video processing device, the video processing device manipulates and scales the image from showing a longitudinal view of the colon's interior surface to showing a "flattened" rectangular view of the colon's interior surface. This procedure, illustrated in FIGS. 3a to 3g, may be carried out by excising the image so that it shows only the interior surface of a given length of the colon. FIG. 3a illustrates an image 40 captured by the imaging device 32 and relayed to the video processing device. As a first step, as shown in FIG. 3b, the processing device outlines the lumen 42 by analyzing the image 40 for the difference in contrast between the colon's lumen 42 and its interior surface 44. After it has outlined the lumen 42, the processing device excises the lumen 42 from the image 40, as shown in FIG. 3c. In some embodiments, both the lumen 42 and the area surrounding the lumen 42 may be excised from the image 40. Then, the outer edge 46 of the image 40 may be excised to produce a ring-shaped image of the colon, as shown in FIGS. 3d and 3e. Preferably, the outer edge of the excised image is similar in shape to its inner edge of the excised image. In other words, the outer edge of the excised image can be equally spaced from the inner edge in the radial direction. This allows the flattened image to have a substantially rectangular configuration. Alternatively, the outer edge of the image can follow the outline of a haustral fold of the colon as shown in FIG. 3d. A haustral fold can be identified by the unique pattern of shading and contrast exhibited in the image.

Figure 3F:
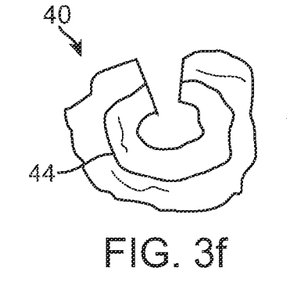
Figure 3G:
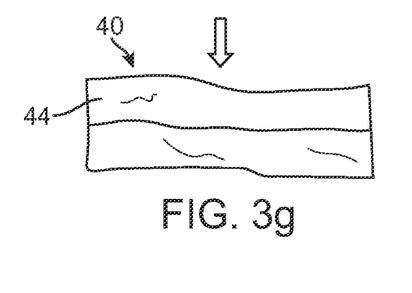

This excised image is then "cut" radially and longitudinally along a side of the image (FIG. 3f), and it is manipulated and flattened to show a rectangular view of the colon's interior surface (FIG. 3g). The excised image may be "cut" with or without overlap. When "cut" with overlap, the two "cut" edges of the image may overlap, and a region of the image may be on both sides of the "cut." To carry out this procedure, the processing device may convert the inner and outer edges of the image into substantially straight lines such that the ring-shaped view is converted into a rectangular view as shown in FIGS. 3f to 3g. This conversion causes certain areas of the image to undergo compression and others expansion.

Figure 4A:
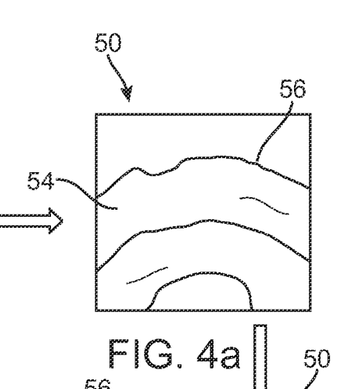
FIGS. 4a to 4g show another example of image transformation.
Figure 4B:
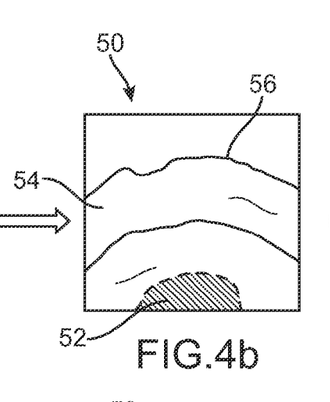
Figure 4C:
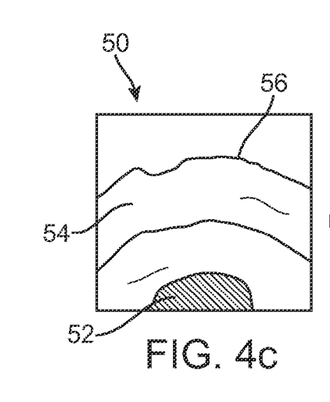
Figure 4D:
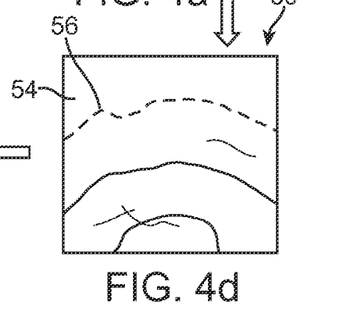
Figure 4E:
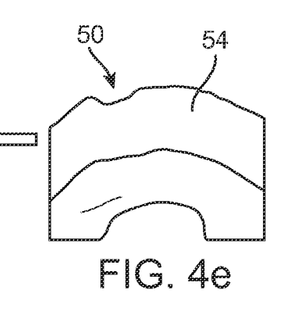
Figure 4F:
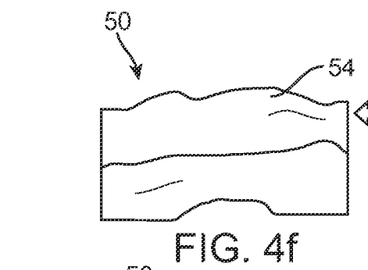
Figure 4G:
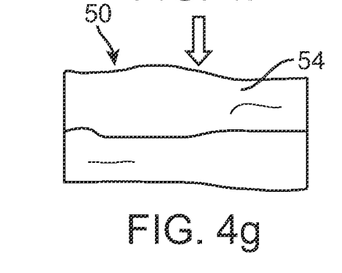

The previous discussion presupposes that the image of the colon shows a longitudinal view of the colon. In other words, the endoscope 10 lies parallel with the longitudinal axis of the colon, and the imaging device 32 of the endoscope 10 is disposed at the distal end 19 of the endoscope 10 and faces the longitudinal direction of the colon. In a situation where the imaging device 32 is angled away from the longitudinal axis of the colon, the image 50 may not show the entire lumen 52, and the image may need to be reconstructed in a slightly different manner (FIGS. 4a to 4g). As seen in FIG. 4a, the lumen 52 or part of the lumen 52 is identified by the difference in contrast. Once the lumen 52 has been identified, it is excised from the image 50 as shown in FIG. 4c, and a corresponding arc is also excised from the outer edge of the image 50 as shown in FIG. 4d. The image 50 is then converted to a substantially rectangle view as shown in FIGS. 4f and 4g.

In a situation where the image does not show the colon's lumen, the processing device may locate the image spatially based on the positions of the previous images, such as the positions of the preceding images. For example, if the imaging device 32 faces a direction that is perpendicular to the longitudinal direction of the colon, the processing device can locate the image based on the positions of the previous images that overlap with this particular image. Images captured from this viewpoint may not need to be converted because of their substantially rectangular and flat shape.

Once an image has been converted into a flat view, the image is analyzed in conjunction with other images, such as the preceding images, to find similar regions and define corresponding key points. This can be accomplished by any one of the various methods known in the field of imaging technology. One such method is an algorithm known as SIFT (Scale Invariant Feature Transform), which is invariant to image scaling, rotations, and partially invariant to changes in illumination and 3D camera viewpoint. Interest points, which are invariant to scale and rotation, are identified in each image by constructing a multi-scale pyramid of Difference of Gaussian (DoG) images. Key points are identified by localizing maxima or minima in the Gaussian pyramid across levels. Next, each interest point is oriented by computing a gradient orientation histogram. A set of orientation histograms in a neighborhood such as 4×4 pixel neighborhood may be used to create the key point descriptor. Finally, the feature descriptors are normalized in order to account for differences in illumination. Once feature points and descriptors are identified in each image, corresponding key points are identified. And, after similar regions or corresponding key points are identified between images, a suitable transformation matrix, which brings the images together such that key points or similar regions overlap, is calculated. An index or number may be used to measure the degree of similarity between two regions of two images. If this index or number is above a given value the two regions of the two images are considered to be overlapping.

Figure 5:
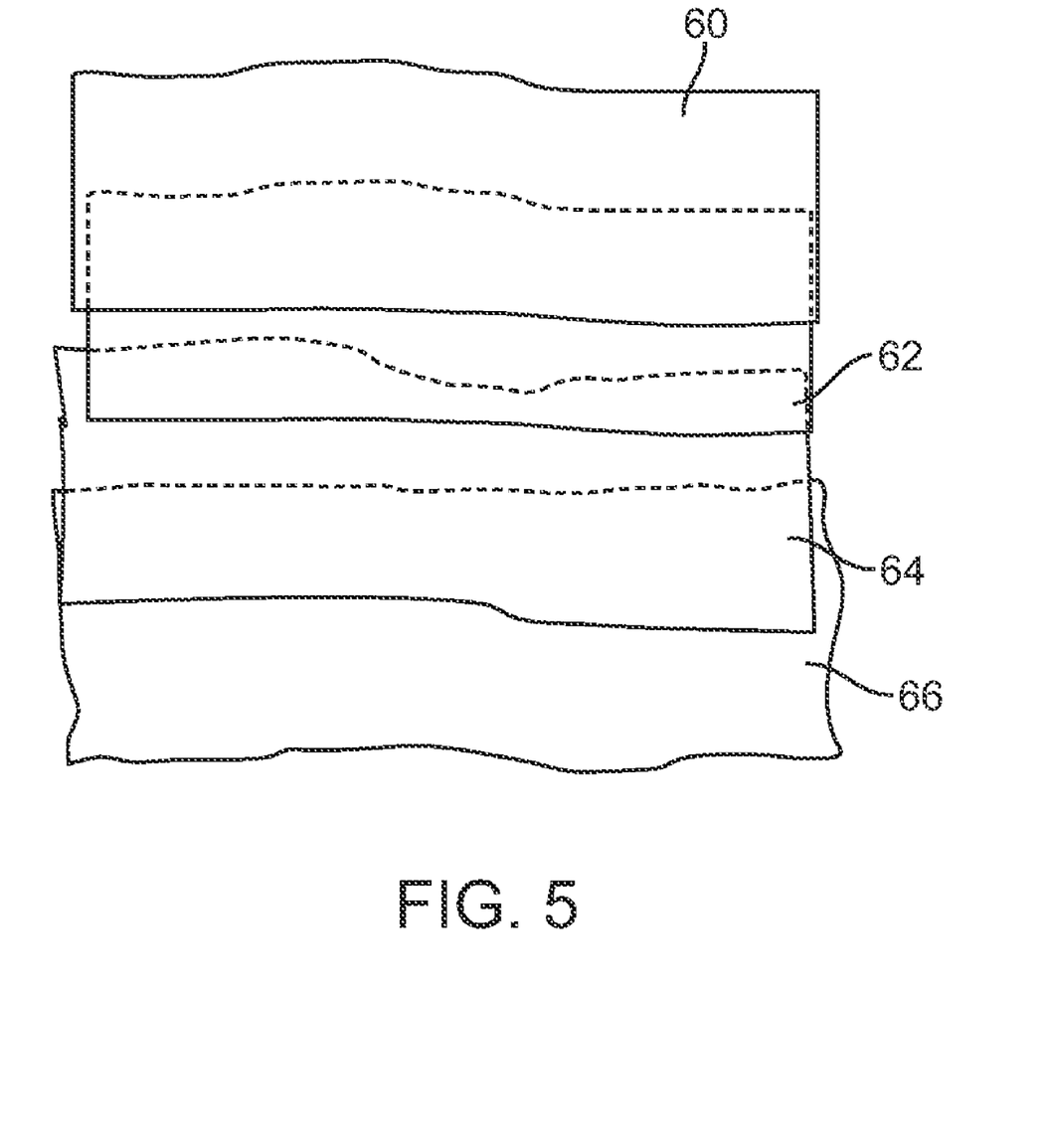
FIG. 5 shows a diagram illustrating the joining of images.

In the final step, two images are joined together by meshing or overlapping the images as dictated by the transformation matrix. Every image thereafter may be then joined to the preceding series of joined images. It is hoped that, by the end of the procedure, a single image that includes a 2-D view of the interior surface of the colon results as shown in FIG. 5, which shows that four partially overlapping images 60, 62, 64, 66 are joined to form a single image.

In another preferred embodiment, to verify that the single joined image of the interior surface of the colon is complete, the processing device checks to ensure that no areas are missing as it continuously joins images together. When an area is missing, the processing device sends a signal, such as an audio and/or visual signal, that alerts the physician to the missed area. The physician can then return to the missing area and capture one or more additional images. In addition, in the event that an image is fuzzy or otherwise unsuitable for the construction of the single joined image, the processing device also alerts the physician so that one or more additional images may be acquired to take the place of the unsuitable image.

A missing area in the joined image can be detected in various manners. For example, there is likely a missing area if an excised inner or outer edge of a partial image is not joined to another partial image or if a region bordering on an excised inner or outer edge of a partial image does not have a corresponding region in another partial image and therefore cannot be joined to another partial image. This, however, does not always apply to the cut edge of a partial image (FIG. 3f), which is made so that the partial image can be flattened (FIGS. 3a-3g). This may also not apply to the first and last images because these two images each have an edge not joined to another image. Another way to detect a missing area is to see whether the cut edges of each partial image can be rejoined after the partial images have been joined to form a single image. If the cut edges of each partial image cannot be rejoined, the single image will likely have a missing area.

Figure 6:
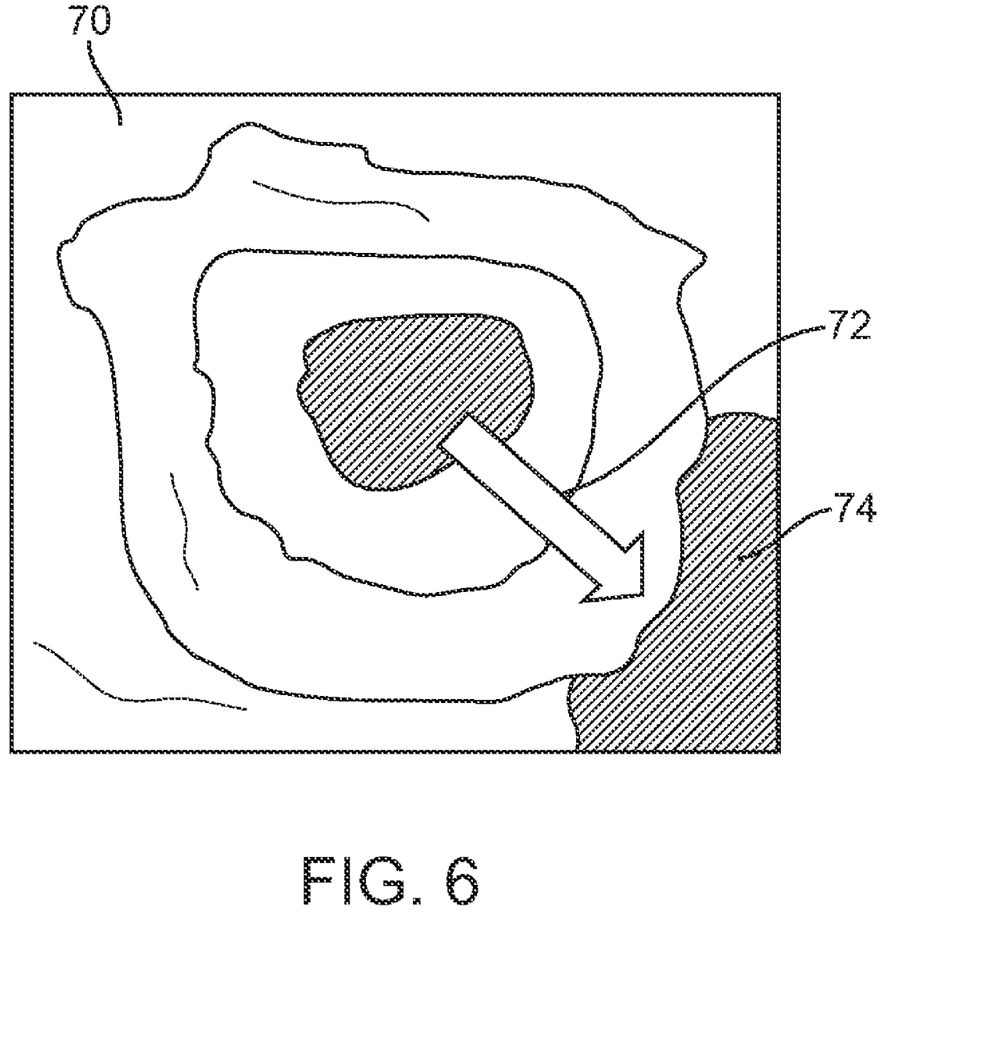
FIG. 6 shows an on-screen cue for directing an operator to a missing area of a joined image.

In another preferred embodiment, when there is a missing area in the single joined image or an unsuitable image, the processing device uses an on-screen navigation cue to direct the operator to the location of the missing area or unsuitable image. As shown in FIG. 6, the on-screen navigation cue may include an arrow 72 on the screen 70 indicating the desired direction of movement for the imaging device 32. Additionally or alternatively, the on-screen navigation cue may include a highlighted area 74 on the screen 70 representing the location of the missing area or unsuitable image. The processing device may implement this feature by comparing the images joined previously with the current image being captured by the imaging device 32. By comparing corresponding key points between these images, the processing device can direct the operator to move the imaging device 32 to the desired location.

In a further preferred embodiment, the processing device can calculate the scanning speed and/of the total amount of time that the imaging device spends in a segment of the colon such as the ascending or transverse portion of the colon. To calculate the scanning speed, the processing device may rely on an algorithm that determines tracking time or speed in a manner similar to an optical computer mouse. The processing device can perform the same or similar steps of analyzing captured images. Before joining the images, the processing device analyzes the distance by which key points or corresponding areas have moved from one image to a subsequent image. The processing device can calculate the scanning speed by dividing the distance traveled by the time lapsed between the two images. The distance by which a given point or feature travels can be denoted by the number of image pixels. Each pixel can then be standardized to a measurement of actual distance such that the calculation can be performed.

The distance traveled can also be calculated by measuring the size change of a geometric feature from one image to another image. For example, if the geometric feature appears larger in an earlier image and smaller in a later image, it can be concluded that the imaging device is moving away from the geometric feature. The distance traveled by the imaging device can be calculated from the change in size.

To calculate the total amount of time spent in a segment of the colon, the processing device needs to recognize when the imaging device is in the segment of the colon. In one preferred embodiment, the processing device recognizes a segment of the colon by its distinctive features, which can be, for example, the various flexures (e.g., splenic, hepatic, etc). Preferably, the processing device recognizes a feature by comparing the captured image of the feature with a stored standard or typical image of the feature. For example, as the endoscope is withdrawn from the end of the colon, the hepatic flexure is expected first, and images are filtered for properties that would suggest an image of the hepatic flexure. The location of areas of shading/contrast and the location of the lumen in the image would suggest to the processing device that the image is of a flexure. The processing device can alert the operator about whether she is scanning the colon too fast and provide data on how much time was spent in each segment of the colon.

Another feature that can be used to recognize the segment of the colon is the geometric shape of the colon. For example, the lumen of the transverse colon has a particularly triangular shape. An image of the colon's geometric shape can be compared with a database of images the colon's geometric shape to determine which segment of the colon the imaging device is in.

In an alternate embodiment of the invention, the endoscope may have a sensor or transducer for communicating the position (such as the location and/or orientation) of the imaging device to the processing device. Examples of such a positioning sensor include magnetic positioning sensors such as the Aurora System manufactured by NDI International of Waterloo, Canada, RF positioning sensors, or optical positioning sensors. The processing device can integrate the positional information of the imaging device with the image capturing and joining algorithm to better determine how to join the images. Joining of the images can be improved based on the imaging device's position, or based on information about the particular geometry of the colon the imaging device is in.

While particular embodiments of the present invention have been shown and described, it will be obvious to those skilled in the art that changes and modifications can be made without departing from this invention in its broader aspects. For instance, the above embodiments involve the examination of a colon. In general, however, a method or device of the present invention can be used to examine any cavity, such as any body cavity. Therefore, the appended claims are to encompass within their scope all such changes and modifications as fall within the true spirit and scope of this invention.

The invention claimed is:

1. A method for examining or imaging an interior surface of a tubular cavity, the method comprising:
   capturing partial images of the interior surface of the cavity;
   joining the captured partial images to form a complete image of said interior surface of the tubular cavity;
   flattening the partial images of the interior surface of the tubular cavity, wherein flattening includes:
      analyzing said partial image for a difference in contrast between a lumen of the tubular cavity and said interior surface of the tubular cavity;
      outlining the lumen of the tubular cavity in said partial image; and
      excising the lumen from said partial image; and
   providing a warning if the joined partial images does not form a complete image of said interior surface of the tubular cavity.

2. The method of claim 1, wherein the step of capturing partial images includes
   storing the captured partial images; and
   recording a sequence in which the partial images are captured.

3. The method of claim 1, wherein the step of joining the captured partial images includes joining the flattened partial images to form a complete flat image of said interior surface of the tubular cavity.

4. The method of claim 1, wherein the step of flattening each partial image includes excising an outer edge of the tubular cavity in said partial image.

5. The method of claim 4, wherein the outer edge of the excised partial image of said interior surface of the tubular cavity is larger than, but similar in shape to, the excised lumen.

6. The method of claim 5, wherein the tubular cavity is a colon, and wherein the outer edge of the excised partial image of the interior surface of the colon coincides with a haustral fold of the colon.

7. The method of claim 5, wherein the step of flattening each partial image includes flattening the excised partial image to create a rectangular image.

8. The method of claim 7, wherein the step of flattening the excised partial image to create a rectangular image includes straightening each of the inner and outer edges of said partial view of said interior surface of the tubular cavity into a substantially straight line.

9. The method of claim 8, wherein the step of joining the captured partial images includes identifying similar regions or corresponding key points between any two images.

10. The method of claim 9, wherein the step of joining the captured partial images includes calculating a suitable transformation matrix which brings the two images together such that the key points or similar regions overlap.

11. The method of claim 10, wherein the step of joining the captured partial images includes joining the two images by meshing or overlapping the images as dictated by the transformation matrix.

12. The method of claim 11, further comprising:
   capturing one or more additional partial images of a missing area in the image of the interior surface of the cavity if the joined partial images do not form a single complete image of said interior surface of the cavity;
   joining the one or more additional partial images with the incomplete single image of said interior surface of the cavity to form a complete image of said interior surface of the cavity; and
   providing a warning if the joined partial images still does not form a single complete image of said interior surface of the cavity.

13. The method of claim 1, wherein the step of joining the captured partial images includes identifying similar regions or corresponding key points between any two images.

14. The method of claim 13, wherein the step of joining the captured partial images includes calculating a suitable transformation matrix which brings the two images together such that the key points or similar regions overlap.

15. The method of claim 14, wherein the step of joining the captured partial images includes joining the two images by meshing or overlapping the images as dictated by the transformation matrix.

16. The method of claim 15, further comprising:
capturing one or more additional partial images of a missing area in the image of the interior surface of the tubular cavity if the joined partial images does not form a complete image of said interior surface of the tubular cavity;
joining the one or more additional partial images with the incomplete image of said interior surface of the tubular cavity to form a complete image of said interior surface of the tubular cavity; and
providing a warning if the joined partial images still does not form a complete image of said interior surface of the tubular cavity.

17. The method of claim 1, further comprising:
capturing one or more additional partial images of a missing area in the image of said interior surface of the tubular cavity if the joined partial images does not form a complete image of said interior surface of the tubular cavity;
joining the one or more additional partial images with the incomplete image of said interior surface of the tubular cavity to form a complete image of said interior surface of the tubular cavity; and
providing a warning if the joined partial images including the one or more additional partial images still does not form a complete image of said interior surface of the tubular cavity.

18. The method of claim 17, further comprising providing direction to an operator to reach the missing area.

19. The method of claim 18, wherein the step of providing direction includes using an on-screen navigation cue to direct the operator to the missing area.

20. The method of claim 19, wherein the on-screen navigation cue includes an arrow and the missing area, both of which are displayed on a screen, and wherein the arrow directs the operator towards the missing area.

21. The method of claim 1, further comprising calculating a scanning speed.

22. The method of claim 21, wherein the step of calculating the scanning speed includes identifying similar regions or corresponding key points between two images; calculating a distance by which a key point or corresponding area has moved from the earlier one of the two images to the later of the two images; and calculating the scanning speed by dividing the distance by the time lapsed between the two images.

23. The method of claim 22, wherein the step of calculating the distance includes counting the number of image pixels by which the key point or corresponding area has moved.

24. The method of claim 21, further comprising providing a warning if the scanning speed is greater than a given value.

25. The method of claim 1, further comprising calculating an amount of time spent on examining a region of said interior surface of the tubular cavity.

26. The method of claim 25, further comprising recognizing known features of said interior surface of the tubular cavity to determine the region being examined.

27. The method of claim 25, further comprising providing a warning if the amount of time spent on examining the region is less than a given value.

28. A method for examining or imaging an interior surface of a cavity, the method comprising:
capturing partial images of the interior surface of the cavity;
joining the captured partial images to form a complete image of said interior surface of the cavity;
flattening the partial images of the interior surface of the cavity, wherein flattening includes:
analyzing said partial image for a difference in contrast between a lumen of the cavity and said interior surface of the cavity;
outlining the lumen of the cavity in said partial image; and
excising the lumen from said partial image;
capturing one or more additional partial images of a missing area in the image of said interior surface of the cavity if the joined partial images does not form a complete image of said interior surface of the cavity; and
joining the one or more additional partial images with the incomplete image of said interior surface of the cavity to form a complete image of said interior surface of the cavity.

29. The method of claim 28, further comprising providing direction to an operator to reach the missing area.

30. The method of claim 29, wherein the step of providing direction includes using an on-screen navigation cue to direct an operator to the missing area.

31. The method of claim 30, wherein the on-screen navigation cue includes an arrow and the missing area, both of which are displayed on a screen, and wherein the arrow directs the operator towards the missing area.

32. A method for examining or imaging an interior surface of a colon, the method comprising:
capturing partial images of the interior surface of the colon; and
joining the captured partial images to form a complete image of said interior surface of the colon, wherein each partial image is a partial image of said interior surface of the colon, and wherein the step of joining the captured partial images includes flattening the partial images of the interior surface of the colon, the flattening of each of the partial images including:
outlining the lumen of the colon in said partial image by analyzing said partial image for a difference in contrast between a lumen of the colon and said interior surface of the colon; and
excising the lumen from said partial image.

33. The method of claim 32, wherein the step of joining the captured partial images includes joining the flattened partial images to form a complete flat image of said interior surface of the colon.

34. The method of claim 32, wherein the step of flattening each partial image includes excising an outer edge of the colon in said partial image.

35. The method of claim 34, wherein the excised outer edge of said interior surface of the colon is larger than, but similar in shape to, the excised lumen.

36. The method of claim 35, wherein the outer edge of the excised partial image of the interior surface of the colon coincides with a haustral fold of the colon.

37. The method of claim 35, wherein the step of flattening each partial image includes flattening the excised partial image to create a rectangular image.

38. The method of claim 37, wherein the step of flattening the excised partial image to create a rectangular image includes straightening each of the inner and outer edges of said interior surface of the colon into a substantially straight line.

39. The method of claim 38, wherein the step of joining the captured partial images includes identifying similar regions or corresponding key points between any two images.

40. The method of claim 39, wherein the step of joining the captured partial images includes calculating a suitable transformation matrix which brings the two images together such that the key points or similar regions overlap.

41. The method of claim 40, wherein the step of joining the captured partial images includes joining the two images by meshing or overlapping the images as dictated by the transformation matrix.

42. The method of claim 41, further comprising
providing a warning if the joined partial images does not form a complete image of said interior surface of the colon.

43. The method of claim 42, further comprising
capturing one or more additional partial images of a missing area in the image of the interior surface of the colon if the joined partial images does not form a complete image of said interior surface of the colon;
joining the one or more additional partial images with the incomplete image of said interior surface of the colon to form a complete image of said interior surface of the colon; and
providing a warning if the joined partial images still does not form a complete image of said interior surface of the colon.

44. The method of claim 32, further comprising providing a warning if the joined partial images do not form a complete image of said interior surface of the colon.

45. The method of claim 44, further comprising:
capturing one or more additional partial images of a missing area in the image of the interior surface of the colon if the joined partial images does not form a complete image of said interior surface of the colon;
joining the one or more additional partial images with the incomplete image of said interior surface of the colon to form a complete image of said interior surface of the colon; and
providing a warning if the joined partial images still does not form a complete image of said interior surface of the colon.

46. A method for using an imaging device to examine or image an interior surface of a cavity, the method comprising:
using an imaging device to capture partial images of the interior surface of the cavity;
using a position sensor coupled to the imaging device to determine a position of each partial image; and
using the positions of the partial images to assist in joining of the partial images to form a complete image of said interior surface of the cavity, wherein the joining includes flattening the partial images of the interior surface of the cavity, wherein flattening includes:
analyzing said partial image for a difference in contrast between a lumen of the cavity and said interior surface of the cavity;
outlining the lumen of the cavity in said partial image; and
excising the lumen from said partial image.

47. A device for examining or imaging an interior surface of a cavity, the device comprising:
an imaging device configured to capture partial images of the interior surface of the cavity; and
a processing device configured to join the captured partial images to form a complete image of said interior surface of the cavity, the processing device being configured to provide a warning if the joined partial images do not form a complete image of said interior surface of the cavity, wherein the processing device is configured to flatten the partial images of the interior surface of the cavity by:
analyzing said partial image for a difference in contrast between a lumen of the cavity and said interior surface of the cavity;
outlining the lumen of the cavity in said partial image; and
excising the lumen from said partial image.

48. A device for examining or imaging an interior surface of a cavity, the device comprising:
an imaging device configured to capture partial images of the interior surface of the cavity; and
a processing device configured to join the captured partial images to form a complete image of said interior surface of the cavity, wherein the imaging device is configured to capture one or more additional partial images of a missing area in the image of said interior surface of the cavity if the joined partial images do not form a complete image of said interior surface of the cavity, the processing device being configured to join the one or more additional partial images with the incomplete image of said interior surface of the cavity to form a complete image of said interior surface of the cavity, wherein the processing device is configured to flatten the partial images of the interior surface of the cavity by:
analyzing said partial image for a difference in contrast between a lumen of the cavity and said interior surface of the cavity;
outlining the lumen of the cavity in said partial image; and
excising the lumen from said partial image.

49. A device for examining or imaging an interior surface of a colon, the device comprising:
an imaging device configured to capture partial images of the interior surface of the colon; and
a processing device configured to join the captured partial images to form a complete image of said interior surface of the colon, wherein the processing device is configured to flatten the partial images of the interior surface of the colon by:
analyzing said partial image for a difference in contrast between a lumen of the colon and said interior surface of the colon;
outlining the lumen of the colon in said partial image; and
excising the lumen from said partial image.

50. A method for examining or imaging an interior surface of a cavity, the method comprising:
capturing partial images of the interior surface of the cavity;
joining the captured partial images to form a complete image of said interior surface of the cavity, wherein the joining includes flattening the partial images of the interior surface of the cavity, wherein flattening includes:
analyzing said partial image for a difference in contrast between a lumen of the cavity and said interior surface of the cavity;
outlining the lumen of the cavity in said partial image; and excising the lumen from said partial image; and storing the complete image as a single two dimensional image representation of the cavity.

51. The method of claim 50, wherein the complete image is used for medical document recording purposes.

52. The method of claim 50, wherein two or more complete image stored at different time intervals is used to monitor relative changes in the cavity between the time intervals.

* * * * *